United States Patent [19]

Liu

[11] Patent Number: 5,990,478

[45] Date of Patent: Nov. 23, 1999

[54] METHOD FOR PREPARING THIN SPECIMENS CONSISTING OF DOMAINS OF DIFFERENT MATERIALS

[75] Inventor: Chin-Kai Liu, Taichung, Taiwan

[73] Assignee: Taiwan Semiconductor Manufacturing Co. Ltd., Hsin-Chu, Taiwan

[21] Appl. No.: 08/889,953

[22] Filed: Jul. 10, 1997

[51] Int. Cl.[6] .................................................. G01N 1/32

[52] U.S. Cl. .......................... 250/307; 250/304; 216/38; 216/39; 204/192.34

[58] Field of Search .................................. 250/307, 304; 216/38, 39; 204/192.34

[56] References Cited

U.S. PATENT DOCUMENTS

| 5,498,871 | 3/1996 | Koo et al. ................................ 250/307 |
| 5,563,412 | 10/1996 | Zandbergen et al. .................. 250/307 |
| 5,892,225 | 4/1999 | Okihara ................................... 250/307 |

*Primary Examiner*—Jack I. Berman
*Attorney, Agent, or Firm*—Tung & Associates

[57] ABSTRACT

The present invention discloses a method for preparing thin specimens suitable for physical analysis of a semiconductor microstructure by an instrument such as a transmission electron microscope. The method can be practiced by first forming support structures in a low density material medium for shielding a higher density material to be analyzed such that materials having different densities may be removed in a subsequent ion milling process at approximately the same milling rate with the lower density material supporting the higher density material during the ion milling process.

20 Claims, 1 Drawing Sheet

METHOD FOR PREPARING THIN SPECIMENS CONSISTING OF DOMAINS OF DIFFERENT MATERIALS

FIELD OF THE INVENTION

The present invention generally relates to a method for preparing thin specimens consisting of domains of different materials and more particularly, relates to a method for preparing thin specimens consisting of domains of different materials by first forming support structures in a lower density material for supporting a higher density material during a material removal process.

BACKGROUND OF THE INVENTION

In the study of electronic materials and processes for fabricating such materials into electronic devices, a thin specimen is frequently required for analysis and for process validation. For instance, thin specimens are frequently used in the analysis of semiconductor structures by a transmission electron microscopy (TEM) method. TEM is one of the more popular methods used in analyzing the microscopic structures of semiconductor devices. The advantages achieved by a TEM method over that of a scanning electron microscopy (SEM) method are higher magnification and simpler specimen preparation since no staining is required, even though a more three dimensional image can be obtained by the SEM method.

In preparing thin specimens of semiconductor structures for a TEM investigation, various polishing and milling processes are involved so that specimens having thicknesses less than 1 $\mu$m can be obtained. As device dimensions are continuously being reduced to the sub-half-micron level, the use of thin specimens for study by the TEM method becomes more important. In general, when a thin specimen is prepared for a TEM study, various mechanical polishing methods are first used to bring the dimension of the specimen down to its approximate dimension. A final sample preparation process is then accomplished by a method called ion milling. The ion milling method is frequently conducted by a focused ion beam (FIB) technique. In the FIB technique, focused ion beams are used to either locally deposit or remove materials. A cluster of ionized beam consists of an aggregate of 100 to 2,000 atoms. When the cluster impacts on the surface of a semiconductor structure, the cluster disintegrates into atoms which are then scattered over the surface and deposit to form a film. The technique can be used to deposit single crystal metals such as epitaxial aluminum on a silicon substrate or single crystal oxides such as silicon oxide on a silicon surface.

Focused ions beams have also been used in a wide range of applications for restructuring semiconductor circuits after they have been fabricated. For instance, the restructuring process includes mask repairing, micromachining, device cross-sectioning and fabrication of structures with dimensions less than 100 nm. Typical ion beams have a focused spot size of smaller than 100 nm produced by a high intensity source. Sources of such high intensity ions are either liquid metal ion sources or gas field ion sources. Both of these sources have a needle type form that relies on field ionization or evaporation to produce the ion beam. After the ion beam is produced, it is deflected in a high vacuum and directed to a desired area without requiring a masking step.

The focused ion beams can be used in the semiconductor processing industry as a cutting or attaching method when performing circuit repair, mask repair or micromachining processes. A cutting process can be performed by locally sputtering the material with a focused ion beam while the attaching process can be performed by a focused ion beam induced deposition process. For instance, a tungsten deposition process is typically used to connect metal lines by directing a focused beam of gallium ions to the region to be connected in an environment of hexacarbonyltungsten. In the process, the gallium ions cause the decomposition of hexacarbonyltungsten so that tungsten deposits locally at the desired location. The technique can also be used in a local rewiring process by etching a hole in the oxide and then locally depositing tungsten without shorting to any adjacent conductors.

In an ion beam milling process, when a material is selectively etched by a beam of ions such as $Ga^+$ that is focused to a sub-micron diameter, the technique is often referred to as focused ion beam (FIB) etching or milling. FIB milling is a very useful technique for restructuring a pattern on a mask or an integrated circuit, and for diagnostic cross-sectioning of microstructures. In a typical FIB assisted etching process, a beam of ions such as $Ga^+$ is incident on a surface to be etched and can be deflected to produce a desirable pattern. In the etch chamber, a gas such as $Cl_2$ can be introduced to fill the chamber to about 30 m Torr, while the vacuum outside the chamber where the FIB is generated is normally maintained at approximately $10^{-7}$ Torr. In this sample system, the etch rates for both Si and GaAs have been increased. For instance, the etch rate of GaAs in a $Cl_2$ environment by the FIB technique is about 10 times higher than the etch rate occurred in a chamber without the $Cl_2$ gas. It is theorized that, similar to a reactive ion etching process, chemical reactions are induced or accelerated by the impact of a focused beam of energetic ions. The spatial resolution of the process is frequently limited by the spot size of the focused ion beam that can be produced.

While the technique of FIB micromachining has been used in preparing thin specimens of semiconductor devices, problem occurs when a focused ion beam is used to bombard a device surface that contains domains of different materials that have different densities. This occurs even when the angle of ion bombardment is very low, i.e., between 0° and 5°, as long as there is a large difference between the densities of the two materials. One of such structures can be found in a semiconductor device which has a via or plug formed of a refractory metal in a dielectric material matrix formed of silicon oxide. Since the density of a refractory metal, i.e., tungsten, titanium, etc., is significantly higher than the density of a dielectric material, the sputtered ion beam used in an ion milling process removes the dielectric material at a higher rate than for the refractory metal.

It is known that the etch rates of different semiconductor materials is directly proportional to its densities, a lower density material such as silicon oxide is normally etched at a much higher etch rate than a higher density material such as tungsten. The great disparity in the etch rates leads to a significant processing difficulty in that before a refractory metal plug is micromachined to a desirable thickness, the surrounding silicon oxide material has already been completely etched away, or being etched to such a small thickness that it cracks or breaks. The refractory metal plug is therefore completely unsupported by the dielectric material that it was embedded in. The preparation of a refractory metal plug specimen that is thin enough for the electrons to penetrate through during a TEM examination is therefore extremely difficult.

It is therefore an object of the present invention to provide a method for preparing thin specimens consisting of domains of materials of different densities that does not have the drawbacks and shortcomings of the conventional preparation methods.

It is another object of the present invention to provide a method for preparing thin specimens consisting of domains of materials of different densities and consequently, of different etch rates.

It a further object of the present invention to provide a method for preparing thin film specimens consisting of domains of different materials by a focused ion beam milling technique.

It is another further object of the present invention to provide a method for preparing thin specimens consisting of domains of different materials by a FIB milling technique wherein support structures are first built to support a domain of material that has high density and low etch rate.

It is still another object of the present invention to provide a method for preparing thin specimens consisting of domains of different materials by a FIB milling technique by first forming two cavities in the domain of material that has low density and then depositing a high density material in the cavities.

It is yet another object of the present invention to provide a method for preparing thin specimens consisting of domains of different materials by a FIB milling technique wherein two support structures are first built juxtaposed to a domain of material that has high density such that the domain can be adequately supported during the milling process.

It is still another further object of the present invention to provide a method for preparing thin specimens consisting of domains of different materials by a FIB milling technique in which a domain of a tungsten plug is embedded in a domain of silicon oxide.

It is yet another further object of the present invention to provide a method for preparing thin specimens consisting of domains of different materials by a FIB milling technique wherein a platinum support structure is first built juxtaposed to a tungsten plug for supporting the plug during a subsequent milling process.

SUMMARY OF THE INVENTION

In accordance with the present invention, a method for preparing thin specimens suitable for examination by a transmission electron microscope that consist of domains of materials of different densities is provided. In the method, at least two cavities are first formed adjacent to the domain of material which has a high density and then filling the cavities with a high density material forming support structures such that when the domain of high density material embedded in a low density material is etched, the support structures support the domain of high density material such that all materials are etched at a similar etch rate.

In a preferred embodiment, a method for preparing thin specimens consisting of domains of materials having different densities is provided by the operating steps of first providing a specimen consisting of a first material having a first density embedded in a second material having a second density, the first density is higher than the second density, and then forming at least two cavities in the second material juxtaposed to the first material wherein the at least two cavities have cross-sectional areas in a horizontal plane larger than a cross-sectional area in the same horizontal plane of the first material, the at least two cavities are situated at positions sufficient to support the first material during a subsequent milling step, then depositing a third material which has a third density in the at least two cavities, the third density is higher than the second density, and then finally removing the first, the second and the third material in a vertical plane from the specimen at substantially the same etch rate while the first material is supported by the third material during the removal step.

In another preferred embodiment, a method for preparing a thin specimen of a semiconductor device is provided which includes the operating steps of first providing a semiconductor device that has a refractory metal plug embedded in a dielectric material, the plug has an axis in a vertical plane, then forming two cavities in the dielectric material juxtaposed to and surrounding the refractory metal plug, then depositing a third material which has a density higher than that of the dielectric material in the two cavities, and then removing the refractory metal, the dielectric material and the third material simultaneously until a vertical plane is exposed in a material removal process.

In still another preferred embodiment, a method for preparing thin specimens consisting of domains of materials of different etch rates by an ion milling process can be carried out by the operating steps of first providing a specimen consisting of a first domain that has a first density embedded in a second domain that has a second density, the first density is higher than the second density, then forming at least two cavities in the second domain juxtaposed to the first domain at locations sufficient to support the first domain during a subsequent milling step, then depositing a third material which has a third density in the at least two cavities, the third density is higher than the second density, and then removing the first, the second and the third material in a vertical plane from the specimen at substantially the same rate while the first material is supported by the third material during such removal step.

BRIEF DESCRIPTION OF THE DRAWINGS

These and other objects, features and advantages of the present invention will become apparent from the following detailed description and the appended drawings in which.

DETAILED DESCRIPTION OF THE PREFERRED AND ALTERNATE EMBODIMENTS

The present invention discloses a method for preparing thin specimens for use in analyzing the microstructures of a semiconductor chip, for instance, in a transmission electron microscope. The method is particularly useful for preparing samples that consist of domains of different materials that have different densities. For instance, a refractory metal via or plug embedded in a dielectric material medium such as silicon oxide. Since a refractory metal has a higher density than an oxide material, the milling rate for the oxide material in a FIB milling process is significantly higher than that for the refractory metal. As a result, the surrounding dielectric material may be completely milled away before a suitable thickness of the refractory metal can be achieved. This leads to an undesirable result wherein the oxide layer is either completely milled away or is milled so thin such that it breaks or cracks and is unable to support a refractory metal film embedded therein.

It is known when preparing specimens for a TEM examination that the specimen must be thinned to a very small thickness, i.e., normally less than 1 μm so that electrons may penetrate through the specimen and thus render the analysis possible. The high density and hardness of a refractory metal such as tungsten necessitates such requirement. The TEM technique is frequently used to study a via or plug structure that is embedded in a multilayer dielectric structure, for instance, up to 5 layers of plugs and dielectric layers in a DRAM device. In each layer of the tungsten plug, there may be a TiN layer on both the top and the bottom of the plug. The TiN layer is used as a buffer layer to stop diffusion, as an etch-stop layer and an anti-reflective-coating layer. It should be noted that the present invention novel method of preparing thin specimens for TEM analysis of a semiconductor structure is not limited to a fixed number of layers of vias or plugs in existence in the structure. The method can be advantageously used for structures that have one layer or two layers of plugs, and can also be used for structures that have five or more layers of plugs.

Figure 1:
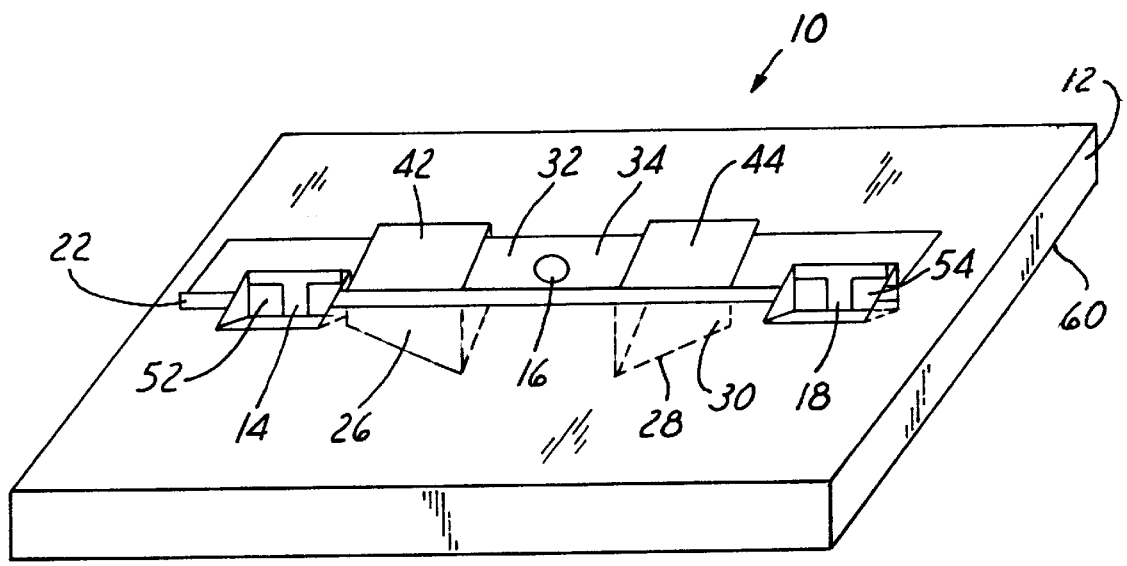
FIG. 1 is a perspective view of a semiconductor structure which incorporates the present invention novel method of building platinum supports juxtaposed to a tungsten plug for the execution of a FIB milling process.

Referring initially to FIG. 1, wherein a perspective view of a present invention semiconductor structure 10 is shown. The semiconductor structure 10 consists of a dielectric layer 12 having a plurality of tungsten plugs 14, 16 and 18 formed therein. The plugs are connected by a metal line 22 of aluminum copper. Tungsten plug 16 is the one that needs to be analyzed for its structure for process validation. The dielectric layer 12 can be suitably formed of a silicon oxide material or of any other dielectric material such as silicon nitride, spin-on-glass, etc.

The present invention novel method for preparing thin specimens consisting of domains of different materials, i.e., a tungsten domain in a silicon oxide domain, can be carried out by the following operating procedure. First, a plurality of plugs or vias are selected for analysis, such as plugs 14–18 that are connected by aluminum copper line 22 shown in FIGS. 1 and 2. Two cavities 26 and 28, one on each side of the tungsten plug 16 are then formed by a FIB etching process. The cavities 26 and 28 are formed through the aluminum copper line 22 into the dielectric layer 12 and are usually formed with an inclined bottom surface. It should be noted that the locations of the cavities should be sufficiently close to plug 16 to be analyzed. The locations of the two cavities are important since they should be situated to provide adequate support for the tungsten plug 16 during an ion milling process such that when a low incident angle, i.e., between 0° and 5° ion beam is subsequently bombarded on a vertical surface 30 of the semiconductor device 10, the dielectric material at locations 32 and 34 are sufficiently sheltered by a high density material deposited into the cavities 26 and 28.

In the next step of the present invention novel process a material that has higher density than the dielectric material 12 is used to fill the cavities 26 and 28. Ideally, the material should have a density close to that of the tungsten plug 16. The technique used to fill cavities 26 and 28 can be suitably a FIB deposition technique. The material used to fill cavities 26 and 28 can be selected from a wide variety of materials such as PT, Ti, Ta, Co and Ni. The selection of the filling material can be determined by the type of target that is available in the FIB machine such that the process can be simplified by not requiring to change the target. The important requirements for the filler material are that it should have a density higher than that of the dielectric material 12, and preferably should have a density close to that of the plug material, i.e., tungsten, titanium, etc.

After cavities 26 and 28 are filled with a higher density material, the two cavities with the material in it act as support columns for the plug 16 during a subsequent milling process. This eliminates the problem associated with the conventional milling method wherein no support columns are used so that the dielectric material situated at 32 and 34 are etch away at a rate higher than the rate that the tungsten plug 16 is etched. Support columns 42 and 44 shield the plug 16 sufficiently during an ion milling process so that the etch rates for the support columns, the plug, and the dielectric material at 32 and 34 are approximately equal. This enables a very thin layer of tungsten plug 16 to be etched while being supported by the surrounding oxide material. As long as the hardness (or density) of the filling material for cavities 26 and 28 is similar to the hardness of the plug 16, a similar milling rate for the support 42, 44 and the plug 16 can be achieve.

Figure 2:
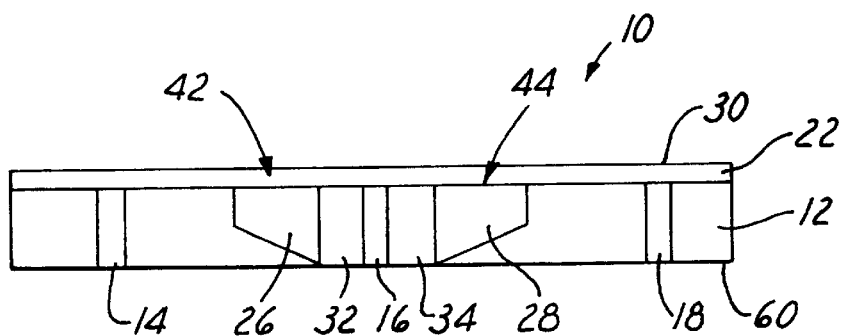
FIG. 2 is a cross-sectional view of the semiconductor structure shown in FIG. 1.

A cross-sectional view of the semiconductor structure 10 of FIG. 1 is illustrated in FIG. 2. It is seen that a thin specimen is obtained by using support structures 42 and 44. The thin specimen can then be examined under a transmission electron microscope to analyze the structure and the quality of the plug 18. The present invention novel method allows a very thin tungsten plug 16 to be obtained while being adequately supported by the dielectric material layer 32, 34 and the support structures 42, 44.

The present invention novel method of preparing thin specimens is started in a prepolishing step by utilizing a mechanical polishing process. Only after the polishing process and a prepolished sample is obtained, the ion milling technique is employed. The ion milling technique is carried out at a very low angle with the surface 30 of the device 10, i.e., between 0 and 5° such that the milling of the surface layer proceeds at a very low rate. The low rate of milling (or etching) allows a precise thickness of the tungsten plug be obtained so that an electron beam can penetrate through the plug and thus producing a high quality image of the plug structure. A suitable thickness of the support structure 42, 44 is less than about 5 μm, preferably less than about 3 μm and more preferably less than about 2 μm. The support structures 42, 44 may have the same depth as the thickness of the dielectric layer 12, or may have a slightly smaller depth at one end forming an inclined bottom surface.

In an alternate embodiment of the present invention novel method for preparing thin specimens for TEM studies, two reference surfaces 52 and 54 are first provided. The reference surfaces 52, 54 are provided by digging holes on both sides of the tungsten plug 16 to be studied and preferably outside the support structures 42, 44. The forming of the two reference surfaces 52 and 54 can be achieved by a FIB method and conducted in the same machine for forming cavities 26, 28. After tungsten plugs 14, 18 are etched to their largest width, i.e., etched to the center point of the plug, the etching process for the reference surfaces is stopped. The surfaces are used in a later process when the plug 16 to be analyzed is etched by comparing with the width of the plug 14 and 18.

The process can be carried out in the following manner. First, support structures 42, 44 are formed by filling cavities 26, 28 with a material selected from PT, Ti, Ta, Co and Ni. The semiconductor structure 10 is then mounted between two glass plates on its top surface 30 and its bottom surface 60. A mechanical pre-polishing step is then utilized to polish away the bulk material from the side of the sandwiched structure. The pre-polishing step is stopped after the polished surface approaches the center point of the plug 16 by comparing with the reference surfaces 52, 54 or the plug width of 14, 18. At this time, the thinning process is switched to a FIB etch chamber and a low angle, high energy ion beam is used to etch away the vertical surface of the support material, the surrounding dielectric material and the tungsten plug 16. By microscopic observation, when the width of the tungsten plug 16 (see FIG. 2) approaches the width of the tungsten plugs 14 and 18, the ion milling process is stopped while a thin specimen of tungsten plug 16 is still supported by its surrounding oxide layers 32, 34 and its support structures 42, 44. The surrounding oxide layers 32, 34 remain due to the presence of the support structures 42, 44. The present invention novel method of preparing a thin specimen consisting of domains of different materials is therefore amply exemplified by FIGS. 1 and 2 and the above descriptions.

It should be noted that the locations for the support structures 42, 44 are completely optional, as long as the locations support the plug 16 to be analyzed. The distance of the support structures 42, 44 from the plug 16 to be analyzed is also optional as long as excessive etching of the dielectric material at 32 and 34 can be avoided and that, adequate support by the dielectric material of plug 16 is provided. It has been found that the locations of the support structures 42, 44 can be advantageously laid out to surround a plug structure such that they are in a symmetrical relationship. Furthermore, the use of the reference surfaces 52, 54 is also optional, and the use of only one reference surface may be adequate to achieve the same desirable results of the present invention.

While the present invention has been described in an illustrative manner, it should be understood that the terminology used is intended to be in a nature of words of description rather than of limitation.

Furthermore, while the present invention has been described in terms of a preferred and an alternate embodiment, it is to be appreciated that those skilled in the art will readily apply these teachings to other possible variations of the inventions.

The embodiment of the invention in which an exclusive property or privilege is claimed are defined as follows:

I claim:

1. A method for preparing thin specimens consisting of domains of different materials comprising the steps of:
   providing a specimen consisting of a first material having a first density embedded in a second material having a second density, said first density being higher than said second density,
   forming at least two cavities in said second material juxtaposed to said first material, said at least two cavities being situated at locations sufficient to shield said first material in a subsequent milling step,
   depositing a third material having a third density in said at least two cavities, said third density being higher than said second density, and
   removing said first, second and third material in a vertical plane from said specimen at substantially the same rate such that said first material is supported by said third material during said removal step.

2. A method according to claim 1, wherein said third density is substantially the same as said first density.

3. A method according to claim 1, wherein said third material and said first material are the same.

4. A method according to claim 1, wherein said first material being embedded in said second material forming a via or plug for a semiconductor device.

5. A method according to claim 1, wherein said first material is a refractory metal and said second material is a dielectric material.

6. A method according to claim 1, wherein said first material is Ta or Ti and said second material is silicon oxide.

7. A method according to claim 1, wherein said third material is selected from the group consisting of Pt, Ta, Ti, Co and Ni.

8. A method according to claim 1, wherein said step of removing said first, second and third material is carried out in an ion milling process.

9. A method according to claim 1 further comprising the step of forming said at least two cavities to a depth of at least 50Å by a focused ion beam method.

10. A method according to claim 1 further comprising the step of depositing said third material by a focused ion beam method.

11. A method for preparing a thin specimen of a semiconductor structure comprising the steps of:
    providing a semiconductor structure having a refractory metal plug embedded in a dielectric material, said plug having an axis in a vertical plane,
    forming two cavities in said dielectric material juxtaposed to said refractory metal plug,
    depositing a third material having a density higher than the density of said dielectric material in said two cavities, and
    removing said refractory metal, said dielectric material and said third material simultaneously until said vertical plane is exposed in a material removal process.

12. A method according to claim 11, wherein said third material has a density substantially similar to the density of the refractory metal in said refractory metal plug.

13. A method according to claim 11, wherein said refractory metal is Ta or Ti.

14. A method according to claim 11, wherein said dielectric material is silicon oxide or silicon nitride.

15. A method according to claim 11, wherein said third material is selected from the group consisting of Pt, Ta, Ti, Co and Ni.

16. A method according to claim 11 further comprising the step of forming said two cavities in said dielectric material by a focused ion beam method.

17. A method according to claim 11, wherein said material removal process is an ion milling method.

18. A method according to claim 11 further comprising a pre-polishing step prior to said material removal process.

19. A method according to claim 11, wherein said step of depositing a third material is carried out by a focused ion beam method.

20. A method for preparing thin specimens consisting of materials having different etch rates in an ion milling process comprising the steps of:
    providing a specimen consisting of a first material having a first etch rate embedded in a second material having a second etch rate, said first etch rate being higher than said second etch rate,
    forming at least two cavities in said second material juxtaposed to said first material, said at least two cavities being situated at locations sufficient to shield said first material in a subsequent milling step,
    depositing a third material having a third etch rate in said at least two cavities, said third etch rate being higher than said second etch rate, and
    removing said first, second and third material in a vertical plane from said specimen at substantially the same rate while said first material is supported by said third material during said removal step.

* * * * *